(12) United States Patent
Haag et al.

(10) Patent No.: US 9,412,550 B2
(45) Date of Patent: Aug. 9, 2016

(54) ELECTRON BEAM DEVICE, A GETTER SHEET AND A METHOD OF MANUFACTURING AN ELECTRON BEAM DEVICE PROVIDED WITH SAID GETTER SHEET

(75) Inventors: Werner Haag, Lugnorre (CH); Dominique Cloetta, Villars-sur-Glâne (CH); Urs Hostettler, Thun (CH); Benno Zigerlig, Untersiggenthal/AG (CH); Toni Waber, Aefligen (CH)

(73) Assignee: TETRA LAVAL HOLDINGS & FINANCE S.A., Pully (CH)

( * ) Notice: Subject to any disclaimer, the term of this patent is extended or adjusted under 35 U.S.C. 154(b) by 262 days.

(21) Appl. No.: 14/126,036

(22) PCT Filed: Jun. 27, 2012

(86) PCT No.: PCT/EP2012/062456
§ 371 (c)(1),
(2), (4) Date: Dec. 13, 2013

(87) PCT Pub. No.: WO2013/004566
PCT Pub. Date: Jan. 10, 2013

(65) Prior Publication Data
US 2014/0145589 A1     May 29, 2014

Related U.S. Application Data

(60) Provisional application No. 61/525,154, filed on Aug. 18, 2011.

(30) Foreign Application Priority Data

Jul. 4, 2011   (SE) ..................................... 1100521

(51) Int. Cl.
*H01J 17/24*   (2012.01)
*H01J 19/70*   (2006.01)
(Continued)

(52) U.S. Cl.
CPC . *H01J 7/18* (2013.01); *A61L 2/087* (2013.01); *H01J 3/027* (2013.01); *H01J 7/186* (2013.01); *H01J 9/24* (2013.01); *H01J 33/02* (2013.01)

(58) Field of Classification Search
CPC ............ H01J 7/18; H01J 3/027; H01J 33/02; H01J 7/186; H01J 9/24; A61L 2/087
USPC ............... 313/554, 553, 559, 420; 445/31
See application file for complete search history.

(56) References Cited

U.S. PATENT DOCUMENTS

| 3,322,993 A | 5/1967 | Vinopal |
| 4,924,145 A * | 5/1990 | Buschmann ............ H01J 61/28 |
| | | 313/490 |

(Continued)

FOREIGN PATENT DOCUMENTS

| EP | 1675170 A2 | 6/2006 |
| JP | 2004-020232 A | 1/2004 |

(Continued)

OTHER PUBLICATIONS

International Search Report (PCT/ISA/210) mailed on Feb. 5, 2013, by the European Patent Office as the International Searching Authority for International Application No. PCT/EP2012/062456.

(Continued)

*Primary Examiner* — Anh Mai
*Assistant Examiner* — Glenn Zimmerman
(74) *Attorney, Agent, or Firm* — Buchanan Ingersoll & Rooney PC (57) ABSTRACT

An electron beam device has a body provided with an exit window, said body is forming or is at least partly forming a vacuum chamber, the vacuum chamber comprising therein a cathode housing and at least one electron generating filament. At least one getter sheet is provided between the cathode housing and the filament. The invention is further comprising a getter sheet for use in an electron beam device and a method of manufacturing an electron beam device comprising at least one getter sheet.

20 Claims, 4 Drawing Sheets

(51) Int. Cl.
*H01J 61/26* (2006.01)
*H01J 7/18* (2006.01)
*A61L 2/08* (2006.01)
*H01J 3/02* (2006.01)
*H01J 33/02* (2006.01)
*H01J 9/24* (2006.01)

(56) References Cited

U.S. PATENT DOCUMENTS

| | | | | |
|---|---|---|---|---|
| 5,111,054 | A * | 5/1992 | Slingerland | H01J 37/18 250/441.11 |
| 5,898,269 | A * | 4/1999 | Baum | G03F 7/70375 313/530 |
| 6,489,720 | B1 * | 12/2002 | Gofuku | H01J 29/94 313/553 |
| 2004/0238763 | A1 | 12/2004 | Wood | |
| 2005/0225224 | A1 | 10/2005 | Dally et al. | |
| 2006/0132036 | A1 | 6/2006 | Hirose et al. | |
| 2007/0069631 | A1 * | 3/2007 | Guo | H01J 29/94 313/497 |
| 2008/0284971 | A1 * | 11/2008 | Park | G02F 1/133305 349/158 |
| 2009/0237861 | A1 * | 9/2009 | Peterson | H01G 9/08 361/502 |
| 2011/0198513 | A1 * | 8/2011 | Holm | A61L 2/087 250/492.3 |
| 2012/0087842 | A1 | 4/2012 | Kristiansson et al. | |
| 2012/0257721 | A1 * | 10/2012 | Park | H01J 35/20 378/123 |

FOREIGN PATENT DOCUMENTS

WO        2010/040454 A1    4/2010
WO   WO 2010/104439 A1    9/2010

OTHER PUBLICATIONS

Swedish Search Report dated Jan. 13, 2012 for Swedish Application No. 1100521-2.

Office Action issued by the Chinese Patent Office on Aug. 26, 2015 in corresponding Chinese Application No. 201280029981.1 (7 pages).

* cited by examiner

ELECTRON BEAM DEVICE, A GETTER SHEET AND A METHOD OF MANUFACTURING AN ELECTRON BEAM DEVICE PROVIDED WITH SAID GETTER SHEET

FIELD OF THE INVENTION

The present invention relates to an electron beam device, a getter sheet for use in said electron beam device and a method of manufacturing an electron beam device provided with said getter sheet.

BACKGROUND OF THE INVENTION

A typical electron beam device comprises a hermetically sealed, i.e. vacuum tight, body inside which a cathode housing is arranged. The cathode housing comprises a filament which is heated by a current in order for electrons to be produced. The thus produced electrons are accelerated by means of a high-voltage potential and exits through an exit window of the body, typically a thin window foil supported by a support grid. Electron beam devices may be used for several purposes, such as curing of ink or adhesives, or sterilisation of volumes or surfaces. Depending on the application properties such as acceleration voltage, beam profile, shape of the electron beam device will vary. The teachings of the present invention may advantageously be applied to electron beam devices used for sterilization of a web of packaging material, since it may significantly improve the performance of electron beam devices being designed for that purpose. It is to be understood, however that it may be applied to other electron beam devices having a similar construction.

Within the field of sterilization of a web of packaging material, performance factors such as stability, durability and longevity are key issues, once the quality of the sterilization is ensured. All components mentioned and still more may be optimized in order for the electron beam device to produce the desired beam shape under any given circumstances.

The present invention relates to the context of elongate electron beam devices used for treatment of larger surface, such as webs of packaging material used for production of packaging containers. More specifically the present invention relates to improvements of such electron beam devices, in terms of ensuring adequate quality while simplifying assembly of the electron beam device.

A hermetically sealed electron beam device does not contain any vacuum pump for the purpose of keeping the vacuum. A vacuum pump is only used during manufacture of the electron beam device to create the vacuum, thereafter the electron beam device is sealed. To provide the possibility of using less highly rated pumping equipment during manufacture, and to complete and maintain the vacuum in the electron beam device, getters may be used. The term "getter" normally refers to a reactive material which chemically absorbs or binds gaseous molecules to their surface inside vacuum environments. A chemical getter provides a pumping action by a chemical reaction where a chemically active gas combines with a chemically active metal to form a solid compound. Gas molecules such as $H_2$, $CO$, $CO_2$, $O_2$, $N_2$, and $NO_x$, form essentially nonreactive oxides, carbides, and nitrides. Generally, the reactions proceed by dissociative chemisorption followed by a reaction to form the resulting oxide, carbide, or nitride. Hydrogen, $H_2$, compounds seem to be an exception, with the hydrogen being dissociatively chemisorbed then dissolved into the metal bulk. Thus, a getter is able to permanently remove small amounts of remaining gas from the evacuated space.

The use of getters further improves the performance of the electron beam device in terms of high voltage stability and rate of occurrences of arcs. Further, a longer lifetime can be expected.

There are several types of getters. A common type is the non-evaporable getters made of metals, for example zirconium or titanium.

When a non-evaporable getter is exposed to air for handling or loading into the electron beam device the material's surface will react with the surrounding gases. This means that the getter, once installed, is already enclosed in an envelope of oxides, nitrides and carbides. Hence, the getter material is "saturated", i.e. essentially inert and will not provide an active getter-pumping surface. Activation is needed in order to start the pumping action. Activation is performed by exposing the getter to high temperature during a suitable period of time when the electron beam device has been sealed and pumped. The activation process removes the layer of surface oxides, nitrides and carbides, by their diffusion into the bulk of the getter and provides a clean metallic surface ready to react with the impinging gaseous molecules in the vacuum environment. The pumping action will continue until the getter is again "saturated", and a new activation cycle is needed. The operational time of the getter between activation cycles depends on the amount of remaining or potentially leaking gas in the electron beam device.

The pumping action, i.e. the ability of the getter to absorb various gases, varies with the temperature of the getter. High temperatures generally generate a high pumping action.

SUMMARY OF THE INVENTION

An object of the invention has been to provide an electron beam device provided with one or several getter sheets, in which said getter sheets are arranged so that they can be easily and homogenously heated both during manufacture of the electron beam device and during operation of the electron beam device. Said object is achieved by an electron beam device having a body provided with an exit window, said body is forming or is at least partly forming a vacuum chamber, said vacuum chamber comprising therein a cathode housing and at least one electron generating filament, wherein at least one getter sheet is provided between the cathode housing and the filament. The filament has a high temperature both during manufacture and operation, and by placing the getter sheets directly in the heat radiating from the filament it is easily secured that the getter sheets will be correctly activated and will have an essentially optimum working temperature during operation of the electron beam device.

In an embodiment of the invention said body is of elongate shape, said exit window is extending in the longitudinal direction of the tubular body, said cathode housing is of an elongate shape and the at least one electron generating filament is extending along the elongate shape of the cathode housing. This type of electron beam device may be used for sterilizing a wide web of packaging material or for curing ink on wide webs or sheets.

In a presently preferred embodiment the at least one getter sheet is arranged in the cathode housing. The cathode housing is provided with relatively large surfaces that can be made to receive and hold one or several getter sheets at a relatively homogenous distance from the filament. This helps to obtain a homogenous heating of the getter sheets.

In a presently preferred embodiment the getter sheet is arranged to be bent to fit in the cathode housing and to be held in place there by its own spring-back force. In this way there is no need for any bulky, expensive and/or complicated attachment means. Further, mounting can be made in a very time efficient way.

Advantageously, the getter sheet is provided with at least one distance flap for providing a gap between the getter sheet and an inner surface of the cathode housing. Having a gap between the getter sheet and the cathode housing further facilitates a homogenous heating In a presently preferred embodiment the getter sheet has a thickness in the range of 0,025-0,075 mm. Preferably, the getter sheet has a thickness of about 0.05 mm. A thickness in this range is thin enough to be easily bent, but large enough to make up an efficient getter sheet.

In a presently preferred embodiment the cathode housing is formed as an elongate semi-annular shell, and the filament is extending essentially centrally within and along said elongate semi-annular shell. A cathode housing formed as a semi-annular shell with the filament centrally placed therein further facilitates a homogenous heating of the getter sheets.

Advantageously, the getter sheet is of a non-evaporable type. Several types of getters may be used in the electron beam device of the present invention, but the non-evaporable type has proven to work well in electron beam devices. For example, the getter sheet comprises a material from the group IV-A of the periodic system, for example zirconium. Using a getter material of the proposed types makes it possible to remove various important gases, most notably $H_2$, $O_2$, $N_2$, $CO_2$ and $CO$, which are common gases in electron beam devices.

In a presently preferred embodiment one or several getter sheets are arranged along the elongate shape of the cathode housing, the getter sheet or getter sheets being arranged within an electron generating length of the filament. To further secure that a correct activation temperature is reached in the getter sheets they are preferably provided in the direct heat radiation from the filament.

Advantageously, several getter sheets are arranged one after the other along the elongate shape of the cathode housing, the getter sheets being arranged within an electron generating length of the filament. Several sheets are more easy to fit within the cathode housing than one large sheet since for example the presence of strut sections and other components in the cathode housing can be disregarded during the design of the sheets. Several sheets also provides for the possibility of having gaps between the sheets that facilitates circulation in the electron beam device, which is important especially during the process of pumping out air to create vacuum. The risk of trapping gas between the cathode housing and the getter sheets are decreased. Preferably, there is at least a cut-out in the sheet such that gas circulation from the gap between the sheet and the cathode housing is facilitated. This will further increase the possibility of successfully creating vacuum during the manufacture of the electron beam device.

The invention also provides a getter sheet for use in an electron beam device. Said getter sheet comprises a sheet material comprising zirconium or titanium, is provided with at least one distance flap for providing a gap between the getter sheet and a surface of the electron beam device, and is arranged to be bent to fit into a cathode housing of the electron beam device, between the cathode housing and the filament, and to be held in place there by its own spring-back force. The advantages with this type of getter sheet have already been discussed above in relation to the electron beam device.

Further, the invention also provides for a method of manufacturing an electron beam device having a body with an exit window, said body forming or at least partly forming a vacuum chamber, said vacuum chamber comprising therein a cathode housing and an electron generating filament. The method comprises the step of arranging at least one getter sheet between the cathode housing and the filament.

BRIEF DESCRIPTION OF THE DRAWINGS

In the following, a presently preferred embodiment of the invention will be described in greater detail, with reference to the enclosed schematic drawings, in which:

FIG. 4b is a top view of the getter sheet in FIG. 4a.

FIG. 4c is a side view of the getter sheet in FIG. 4a.

DETAILED DESCRIPTION OF A PREFERRED EMBODIMENT

Figure 1:
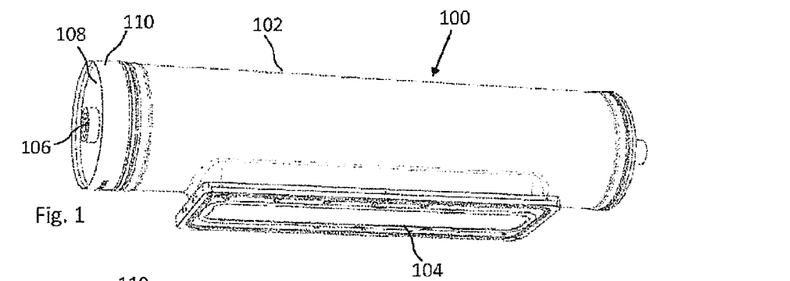
FIG. 1 is a perspective view of an electron-beam device according to one embodiment of the present invention.

FIG. 1 is a perspective view of an exemplary hermetically sealed electron beam device 100 of the present invention, showing only the exterior thereof. The purpose of the drawing is simply to illustrate the basic components of an electron beam device, and it should be emphasized that the purpose is not to provide a true constructional drawing or in any other way limit the present invention.

The main component of the electron beam device is the tubular body 102, which has an elongate shape. An exit window arrangement 104 provides an outlet for electrons from the vacuum inside the tubular body 102. The exit window arrangement 104 in turn comprises subassemblies not relevant for the present invention, yet having the properties of providing an outlet window for electrons while preserving vacuum inside the body 102. A proximal end of the body 102 comprises an assembly including electrical connections 106, and an insulating ceramic disc 108 sealing towards the assembly and an inner perimeter of the body 102. In the present embodiment the ceramic disc 108 actually seals towards the inner perimeter of a cylindrical component 110 which in turn is welded to the elongate body. For reasons not relevant for the present invention this arrangement simplifies assembly, disassembly, and reassembly of the electron beam device.

Figure 2:
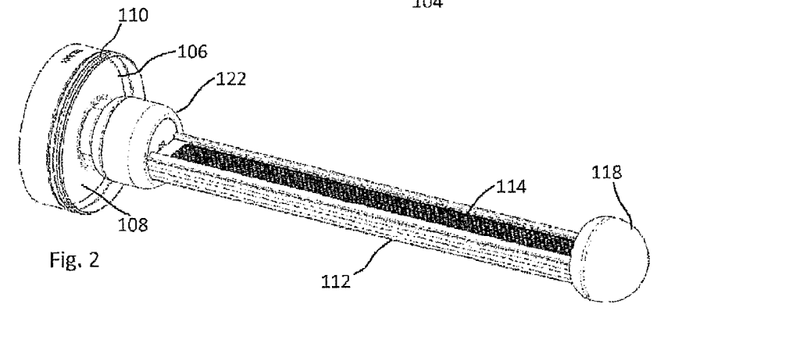
FIG. 2 is a perspective view of the interior of the electron-beam device of FIG. 1.
Figure 3:
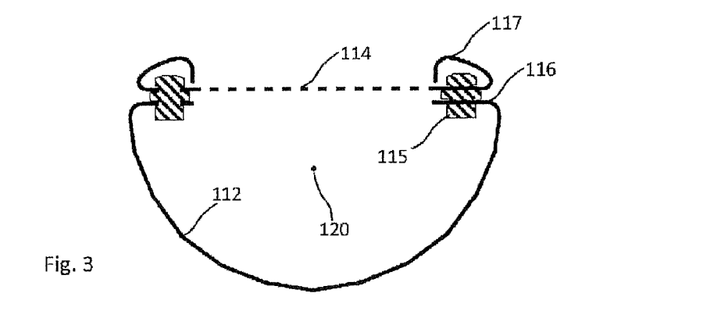
FIG. 3 is a very schematic cross section of the cathode housing, and the control grid of FIG. 2.

Inside the tubular body 102 a cathode housing 112 is arranged, which is one of the components illustrated in FIGS. 2 and 3. The cylindrical component 110 and the ceramic disc 108 are clearly visible, and the skilled person realizes how the illustrated arrangement may be inserted in the tubular body 102 for forming the assembly of FIG. 1. The actual cathode housing 112 is formed as a semi-annular shell, the open side of which is covered by a control grid 114. Inside the annular shell of the cathode housing 112 one or more filaments 120 (see FIG. 3) are arranged, extending from a proximal end of the cathode housing 112 to a distal end thereof. In use, an electron beam is generated by heating the filament 120, using a current, and by accelerating the electron towards the exit window 104 by means of a high-voltage potential.

By applying an electrical potential to the control grid 114 the emission of electrons may be further controlled. If a separate and variable electrical potential is applied to the control grid 114 it makes it possible to use the control grid 114 for active shaping of the generated electron beam. For these purposes the control grid 114 may be electrically connected to a separate power supply (not shown).

The control grid 114, i.e. the open side of the cathode housing 112 should for obvious reasons be facing the exit window arrangement 104. The control grid 114 comprises several openings or through-holes for passage of electrons.

The free longitudinal edges, shown in FIG. 3, of the cathode housing 112 are preferably bent inwards and form radial projections 116. The control grid 114 is attached to the said projections 116 in attachment points 115 which may function as electrical isolators, depending if there is a difference in electrical potential between the cathode housing 112 and the grid 114, or not.

The free longitudinal edges 117 of the control grid 114 is bent in a bulge, or curled, over itself, and in particular over the attachment points 115 between the cathode housing 112 and the control grid 114, for formation of smooth bulges or beads. Said bulges 117 will assist in the generation of a smooth predicable electrical field to the benefit of performance of the electron beam device 100.

The proximal end as well as the distal end of the cathode housing 112 comprises electrical connections as well as physical suspensions for a filament 120. At the distal end this arrangement is housed inside or covered with a dome-shaped cap 118. At its proximal end the cathode housing 112 is suspended in a central opening of the insulating disc 108 and the suspension is also covered by an annular "cap-like" component 122.

Figure 4A:
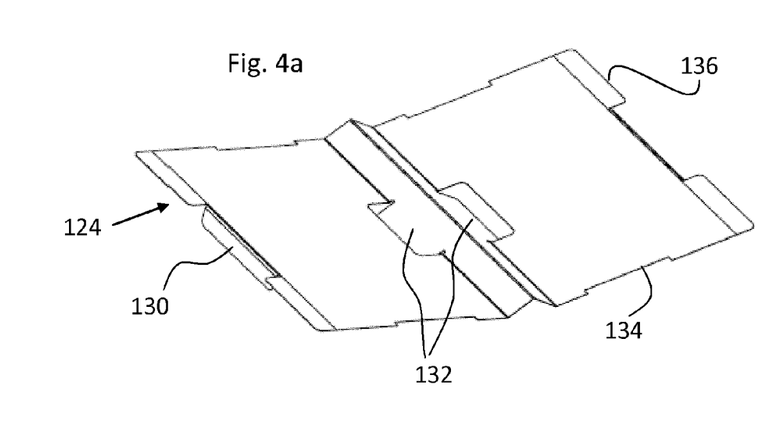
FIG. 4a is a perspective view of the getter sheet according to the invention.
Figure 4B:
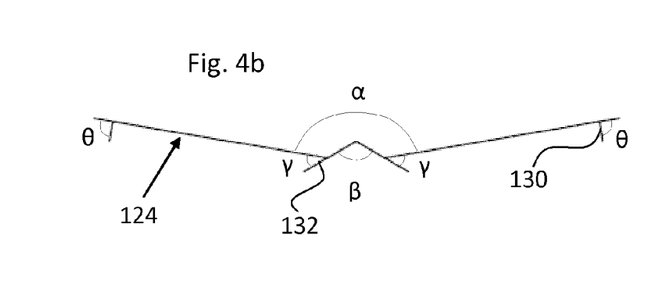
Figure 4C:
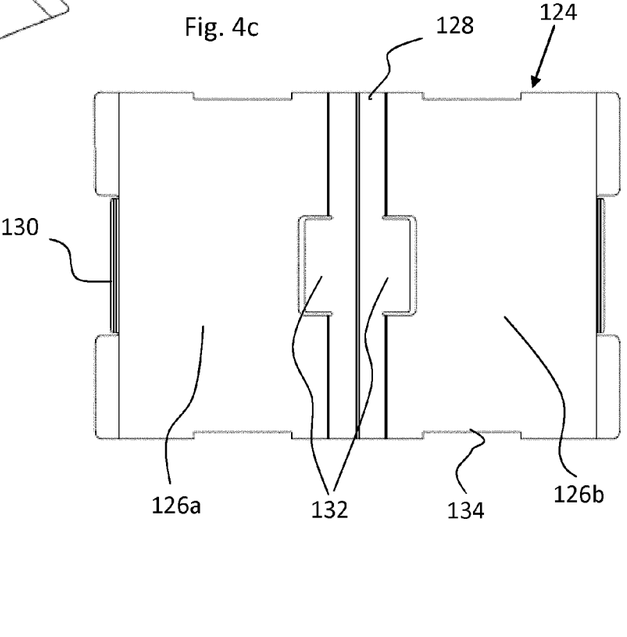

In FIGS. 4a-4c a getter sheet 124 of the invention is shown. There are several types of getters that can be used in a hermetic system like the electron beam device 100 of the present invention. In this embodiment the getter sheet 124 is of the non-evaporable type. Preferably, the material is chosen from the group IV-A of the periodic system. Preferably zirconium (Zr) is used. In another embodiment titanium (Ti), niobium (Nb) or tantalum (Ta) may be used. The getter sheet may also be made up by a base material made of for example molybdenum (Mo), constantan (alloy including 55% copper (Cu) and 45% nickel (Ni)) or stainless steel being coated with a getter material. Possible coating materials are zirconium-aluminum (Zr—Al) or just zirconium (if the base material is molybdenum (Mo)).

The getter sheet 124 is made out of a sheet material and can be manufactured in one piece through for example laser-cutting and a subsequent bending operation. The sheet material has a thickness in the range of 0,025-0,075 mm, preferably a thickness of about 0.05 mm. In this way the getter sheet 124 will be flexible, i.e. will be bendable to fit into the cathode housing 124.

As is shown in FIGS. 4a-4c the exemplary getter sheet 124 is essentially rectangular and comprises a first and a second wing portion 126a, 126b bridged by a central V-shaped interconnection portion 128. The interconnection portion 128 extends from one of the long sides of the rectangular sheet 124 to the other long side. The wing portions 126a, 126b are angled in relation to each other by an angle $\alpha$ in the range of 150-170°. Further, the V-shape of the interconnection portion has an angle $\beta$ of about 110-130°. The two angles $\alpha$, $\beta$ point in two opposite directions giving the getter sheet 124 something like a W-shape. Further, the getter sheets 124 are provided with at least one distance flap for providing a gap between the getter sheet 124 and an inner surface of the cathode housing 112 once mounted. Two cuts are made in each of the short sides of the getter sheet 124, i.e. in the wing portions 126a, 126b, and each centre portion are bent or folded to form a respective outer distance flap 130. Each such outer flap 130 is bent an angle $\theta$ of about 90° in relation to the wings 126a, 126b. Further, two inner flaps 132 are formed by cutting centrally in each respective wing 126a, 126b, from the interconnection portion 128 and in a direction into the wing. These inner flaps 132 will form extensions to the interconnection portion 128 and will be angled an angle $\gamma$ of about 40° in relation to the wings 126a, 126b. Both the inner and outer flaps 130, 132 are protruding from one side of the getter sheet 124, the side that will be facing the inner surface of the cathode housing 112. Furthermore, the getter sheet 124 is provided with one or several cut-outs 134 along its long sides. In this embodiment four cut-outs 134 are made. The cut-outs 134 will serve as circulation gaps between the getter sheets 124 once mounted in the cathode housing 112.

Figure 5:
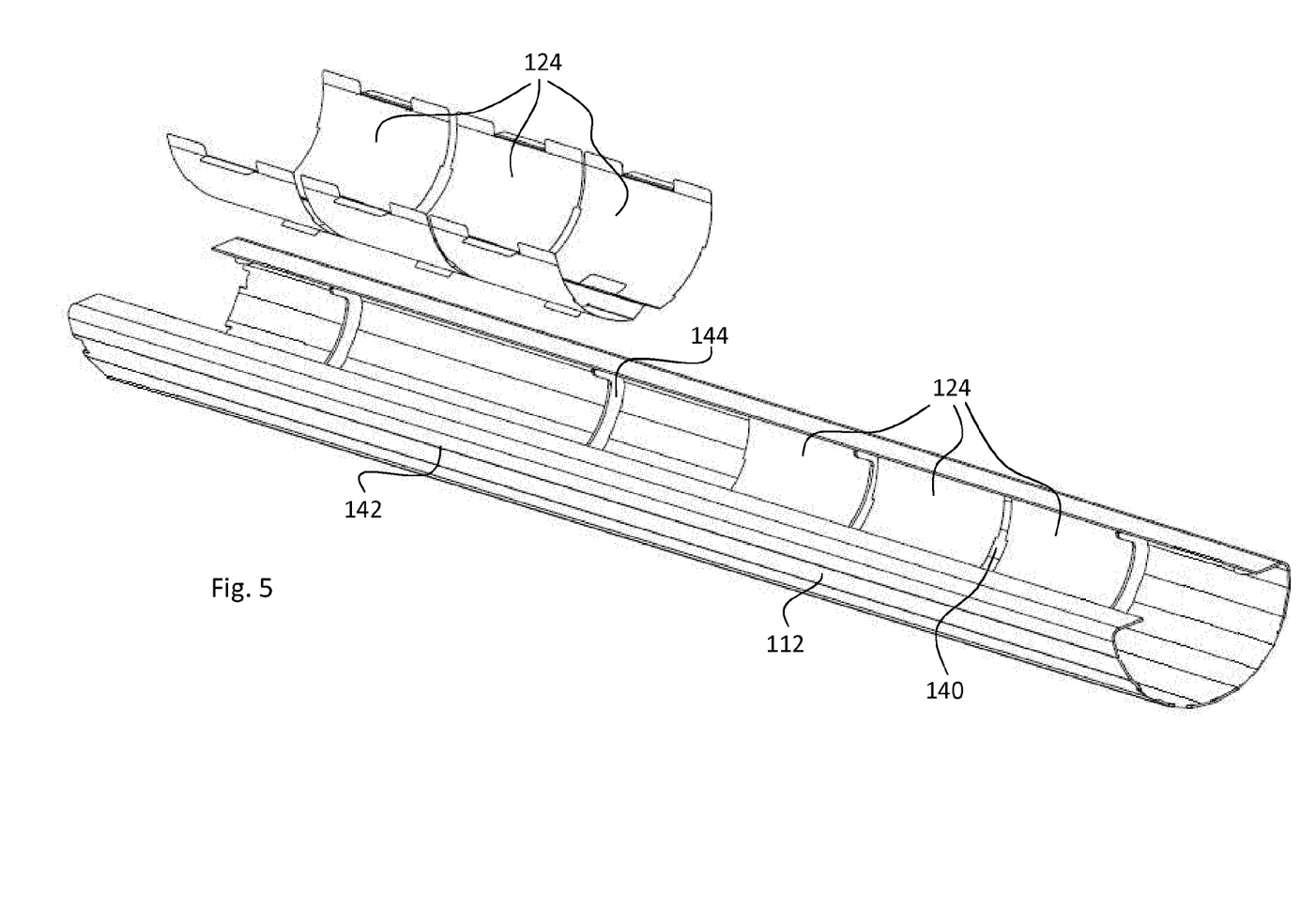
FIG. 5 is a perspective view of the cathode housing and a number of getter sheets according to the invention.
Figure 6:
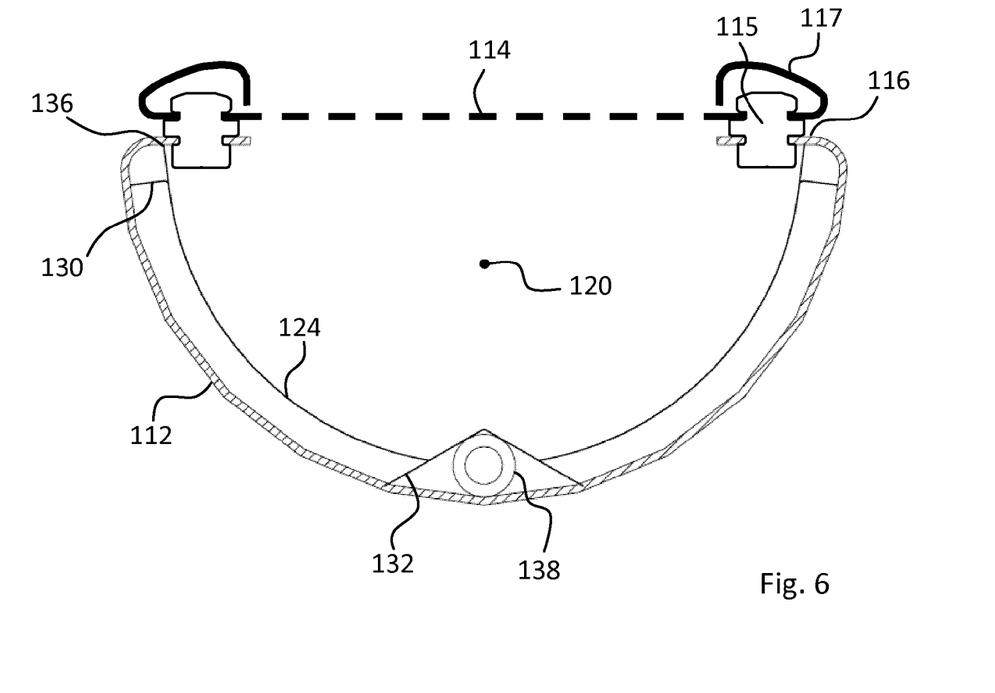
FIG. 6 is a cross section of the cathode housing, the getter sheet, the control grid and the filament.

FIGS. 5 and 6 show the cathode housing 112 with getter sheets 124 fitted therein. The thin sheets 124 are easily bent in a U-shape and fitted in the cathode housing 112, on the inner side of the annular shell. The longitudinal direction of the interconnection portion 128 is aligned with the longitudinal axis of the elongate cathode housing 112. The getter sheets 124 will be held in place in the cathode housing 112 by their own spring-back force. The outer edges 136 of the wings 126a, 126b of the getter sheets 124 will be in contact with an inner surface of the radial projections 116 of the cathode housing 112, on the inside of the control grid attachment points 115, thus preventing the getter sheet 124 to come loose. The edges of the inner and outer flaps 130, 132 of the getter sheet 124 will be in contact with the inner surface of the annular shell of the cathode housing 112, and are thus securing that a distance is provided between the getter sheet 124 and the cathode housing 112. As can be seen in FIG. 6, the inner flaps 132 are positioned one on each side of a tube element 138 provided in the bottom of the cathode housing 112, and the V-shaped interconnection portion 128 bears on said tube element 138.

In FIG. 5 three getter sheets 124 have been mounted one after the other in the cathode housing 112, and another three are shown just above the housing 112, bent and waiting to be inserted therein. It is to be understood that the getter sheets 124 cannot stay in the U-shape as shown in the figure, they are merely shown in that state to facilitate understanding of the invention. The moment a getter sheet 124 of the invention is not held by an external force, it will spring back to its original, un-tensioned shape as shown in FIGS. 4a-c.

As can be seen in FIG. 5 the sheets 124 are placed close to each other and the cut-outs 134 provide gaps 140 facilitating gas circulation from the space delimited by the inner surface of the cathode housing 112 and the getter sheets 124. This prevents any gas to be trapped in that space during manufacture and also during operation.

It is to be understood that any number and size of the getter sheets 124 can be chosen depending on the particular design and size of the cathode housing 112. Preferably, getter sheets 124 are only arranged within the electron generating length of the filament 120. In this way it is possible to ensure homogenous heating of the getter sheets 124 and thereby correct activation and operation. As mentioned in the introduction, heat is necessary to activate the getter sheets 124. During manufacture of the electron beam device 100 the getter sheets 124 are activated by heating the filament 120 to a temperature of about 2100-2500° C. This will in turn heat the getter sheets 124 to a temperature about 670-770° C., which is considered a suitable activation temperature when the getter sheet 124 comprises for example zirconium. During operation of the electron beam device 100, when the filament 120 is heated to about 1700° C. to emit electrons, the getter sheets reach a temperature of about 500-600° C., a temperature at which the absorption of various important gases, most notably $H_2$, $O_2$, $N_2$, $CO_2$ and CO, is good using a getter sheet comprising zirconium. It is also a good temperature to keep re-activating the getter.

In FIGS. 5 and 6 it is apparent that the cross section of the semi-annular shell of the cathode housing 112 is not smoothly rounded, but is formed with facets 142 or as a polygonal chain. This considerably facilitates the bending process used during manufacture of the electron beam device. Further, the cathode housing 112 is made of stainless steel and is provided with a number of strut sections 144 functioning as stiffeners cross the elongate shape of the cathode housing 112. The getter sheets 124 are preferably mounted in between these strut sections 144.

As mentioned the cathode housing 112 and the tubular body 102 are made of stainless steel. The vacuum chamber is further delimited by the insulating disc 108 made of a ceramic material. Preferably, the ceramic material is composed of 97-99.7% $Al_2O_3$ and the remainder $SiO_2$ and CaO.

Alternatively, the cathode housing can be made of nickel.

The getter sheets are arranged into the cathode housing by hand. Since they are thin and may be easily bent the easiest way to insert them is by hand.

Although the present invention has been described with respect to a presently preferred embodiment, it is to be understood that various modifications and changes may be made without departing from the object and scope of the invention as defined in the appended claims.

The invention claimed is:

1. An electron beam device comprising:
   a body provided with an exit window, said body at least partly forming a vacuum chamber;
   a cathode housing disposed in the vacuum chamber and possessing an inner surface;
   at least one electron generating filament disposed in the vacuum chamber;
   at least one getter sheet provided between the cathode housing and the filament, the at least one getter sheet possessing a facing surface facing the inner surface of the cathode housing; and
   a gap between the facing surface of the at least one getter sheet and the inner surface of the cathode housing.

2. The electron beam device according to claim 1, wherein said body is of elongate shape, said exit window extends in the longitudinal direction of the tubular body, said cathode housing is of an elongate shape and the at least one electron generating filament extends along the elongate shape of the cathode housing.

3. The electron beam device according to claim 1, wherein the at least one getter sheet is arranged in the cathode housing.

4. The electron beam device according to claim 1, wherein the at least one getter sheet is arranged to be bent to fit in the cathode housing and to be held in place there by its own spring-back force.

5. The electron beam device according to claim 1, wherein the at least one getter sheet is provided with at least one distance flap providing the gap between the facing surface of the at least one getter sheet and the inner surface of the cathode housing.

6. The electron beam device according to claim 1, wherein the at least one getter sheet possesses a thickness in the range of 0.025-0.075 mm.

7. The electron beam device according to claim 1, wherein the cathode housing is formed as an elongate semi-annular shell, and the at least one filament extends centrally within and along said elongate semi-annular shell.

8. The electron beam device according to claim 1, wherein the at least one getter sheet is non-evaporable.

9. The electron beam device according to claim 1, wherein the at least one getter sheet is arranged along the elongate shape of the cathode housing and within an electron generating longitudinal extent of the filament.

10. The electron beam device according to claim 1, wherein the at least one getter sheet possesses an outer periphery, the at least one getter sheet including an inner flap inwardly spaced from the outer periphery of the at least one getter sheet, the inner flap extending away from the facing surface of the at least one getter sheet in a direction toward the inner surface of the cathode housing.

11. The electron beam device according to claim 5, comprising at least one cut-out in the at least one getter sheet such that gas circulation from the gap between the at least one getter sheet and the cathode housing is facilitated.

12. The electron beam device according to claim 8, wherein the at least one getter sheet comprises a material from the group IV-A of the periodic system.

13. The electron beam device according to claim 9, wherein the at least one getter sheet includes several getter sheets arranged one after the other along the elongate shape of the cathode housing and within an electron generating longitudinal extent of the filament.

14. The electron beam device according to claim 10, wherein the inner flap is a first inner flap and the at least one getter sheet includes a second inner flap, the first and second inner flaps contacting the inner surface of the cathode housing at spaced apart locations.

15. The electron beam device according to claim 12, wherein the at least one getter sheet is made of zirconium.

16. The electron beam device according to claim 14, wherein the at least one getter sheet possesses oppositely located outer peripheral regions, the at least one getter sheet including an outer flap located at each of the outer peripheral regions of the at least one getter sheet, the outer flap extending away from the facing surface of the at least one getter sheet toward the inner surface of the cathode housing.

17. A getter sheet for use in an electron beam device, wherein said getter sheet comprises:
   a sheet material comprising zirconium or titanium;
   the sheet material being provided with at least one distance flap for providing a gap between the getter sheet and a surface of the electron beam device; and
   the getter sheet being configured to be bent to fit into a cathode housing of the electron beam device, between the cathode housing and the filament, and to be held in place there by its own spring-back force.

18. A method for manufacturing an electron beam device comprised of a body with an exit window, said body at least partly forming a vacuum chamber, said vacuum chamber comprising therein a cathode housing and an electron generating filament, the method comprising arranging at least one getter sheet between the cathode housing and the filament, wherein the at least one getter sheet possesses an outer periphery, the at least one getter sheet including an inner flap inwardly spaced from the outer periphery of the at least one getter sheet, and wherein the arranging of the at least one getter sheet between the cathode housing and the filament includes arranging the at least one getter sheet such that a facing surface of the at least one getter sheet faces an inner surface of the cathode housing, and such that the inner flap extends away from the facing surface of the at least one getter sheet in a direction toward the inner surface of the cathode housing.

19. The getter sheet according to claim 17, wherein the getter sheet possesses an outer periphery and a facing surface configured to face an inner surface of the cathode housing, the at least one distance flap including an inner flap inwardly spaced from the outer periphery of the getter sheet, the inner flap being configured such that when the at least one getter sheet is fit into the cathode housing with the facing surface of the getter sheet facing the surface of the electron beam device, the inner flap extends away from the facing surface of the getter sheet in a direction toward the inner surface of the cathode housing.

20. A method for manufacturing an electron beam device comprised of a body with an exit window, said body at least partly forming a vacuum chamber, said vacuum chamber comprising therein a cathode housing and an electron generating filament, the method comprising arranging at least one getter sheet between the cathode housing and the filament, wherein the cathode housing possesses an inner surface, and the arranging of the at least one getter sheet between the cathode housing and the filament includes arranging the at least one getter sheet so that a gap exists between the inner surface of the cathode housing and a surface of the at least one getter sheet that faces the inner surface of the cathode housing.

* * * * *